(12) United States Patent
Hourmand et al.

(10) Patent No.: US 11,882,872 B2
(45) Date of Patent: Jan. 30, 2024

(54) CAPSULES, HEAT-NOT-BURN (HNB) AEROSOL-GENERATING DEVICES, AND METHODS OF GENERATING AN AEROSOL

(71) Applicant: Altria Client Services LLC, Richmond, VA (US)

(72) Inventors: Yannick Hourmand, Haslingfield (GB); Niall Gallagher, Cambridge (GB); Zack Blackmon, Williamsburg, VA (US); Patrick M. Good, Richmond, VA (US); Jarrett Keen, Richmond, VA (US); Rangaraj S. Sundar, Midlothian, VA (US); Eric Hawes, Midlothian, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 678 days.

(21) Appl. No.: 16/838,591

(22) Filed: Apr. 2, 2020

(65) Prior Publication Data
US 2021/0307389 A1    Oct. 7, 2021

(51) Int. Cl.
*A24F 40/42*    (2020.01)
*A24F 40/485*   (2020.01)
(Continued)

(52) U.S. Cl.
CPC .............. *A24F 40/42* (2020.01); *A24F 40/20* (2020.01); *A24F 40/46* (2020.01); *A24F 40/485* (2020.01);
(Continued)

(58) Field of Classification Search
None
See application file for complete search history.

(56) References Cited

U.S. PATENT DOCUMENTS 3,292,634 A * 12/1966 Beucler .................... A24D 1/14
                                                    131/183
8,915,254 B2 * 12/2014 Monsees .............. A61M 11/042
                                                    131/194
(Continued)

FOREIGN PATENT DOCUMENTS

EP          3216357 A1    9/2017
WO    WO-2015/101479 A1    7/2015
(Continued)

OTHER PUBLICATIONS

International Search Report and Written Opinion dated Jun. 7, 2021.
(Continued)

*Primary Examiner* — Phu H Nguyen
(74) *Attorney, Agent, or Firm* — Harness, Dickey & Pierce, P.L.C.

(57) ABSTRACT

A capsule for a heat-not-burn (HNB) aerosol-generating device may include a base of a thermally-conductive material, the base defining a first cavity therein, the base including a first surface, the first surface defining an opening to a second cavity, the first surface including a first plurality of apertures through the first surface. The capsule may further include a cover coupled to the base and on the base, the cover including a second plurality of apertures in a middle portion of the cover, the first plurality of apertures and the second plurality of apertures defining an air flow path through the base and the cover.

22 Claims, 10 Drawing Sheets

(51) Int. Cl.
  A24F 40/46        (2020.01)
  A24F 40/20        (2020.01)
  A61M 15/00        (2006.01)
(52) U.S. Cl.
  CPC ....... *A61M 15/009* (2013.01); *A61M 2205/36* (2013.01)

(56) References Cited

U.S. PATENT DOCUMENTS

| | | | |
|---|---|---|---|
| 9,247,773 | B2 | 2/2016 | Memari et al. |
| 10,179,215 | B2 | 1/2019 | Raichman |
| 10,226,074 | B2 | 3/2019 | Servutas |
| 2011/0186061 | A1 | 8/2011 | Saleh |
| 2017/0020194 | A1 | 1/2017 | Rehders |
| 2017/0099873 | A1 | 4/2017 | Benjamignan et al. |
| 2017/0215485 | A1* | 8/2017 | Zitzke ................ A24F 40/53 |
| 2017/0251718 | A1 | 9/2017 | Armoush et al. |
| 2018/0161246 | A1 | 6/2018 | Davis |
| 2019/0090539 | A1 | 3/2019 | Rostami et al. |
| 2019/0110517 | A1 | 4/2019 | Rogers et al. |
| 2019/0166913 | A1 | 6/2019 | Trzecieski |

FOREIGN PATENT DOCUMENTS

| | | | | |
|---|---|---|---|---|
| WO | WO-2019/012145 | A1 | 1/2019 | |
| WO | WO-2019/243540 | A1 | 12/2019 | |
| WO | WO-2020/020917 | A1 | 1/2020 | |
| WO | WO-2020020917 | A1 * | 1/2020 | ........... A24B 15/243 |

OTHER PUBLICATIONS

International Preliminary Report on Patentability corresponding International Application No. PCT/US2021/021297, dated Sep. 29, 2022.

* cited by examiner

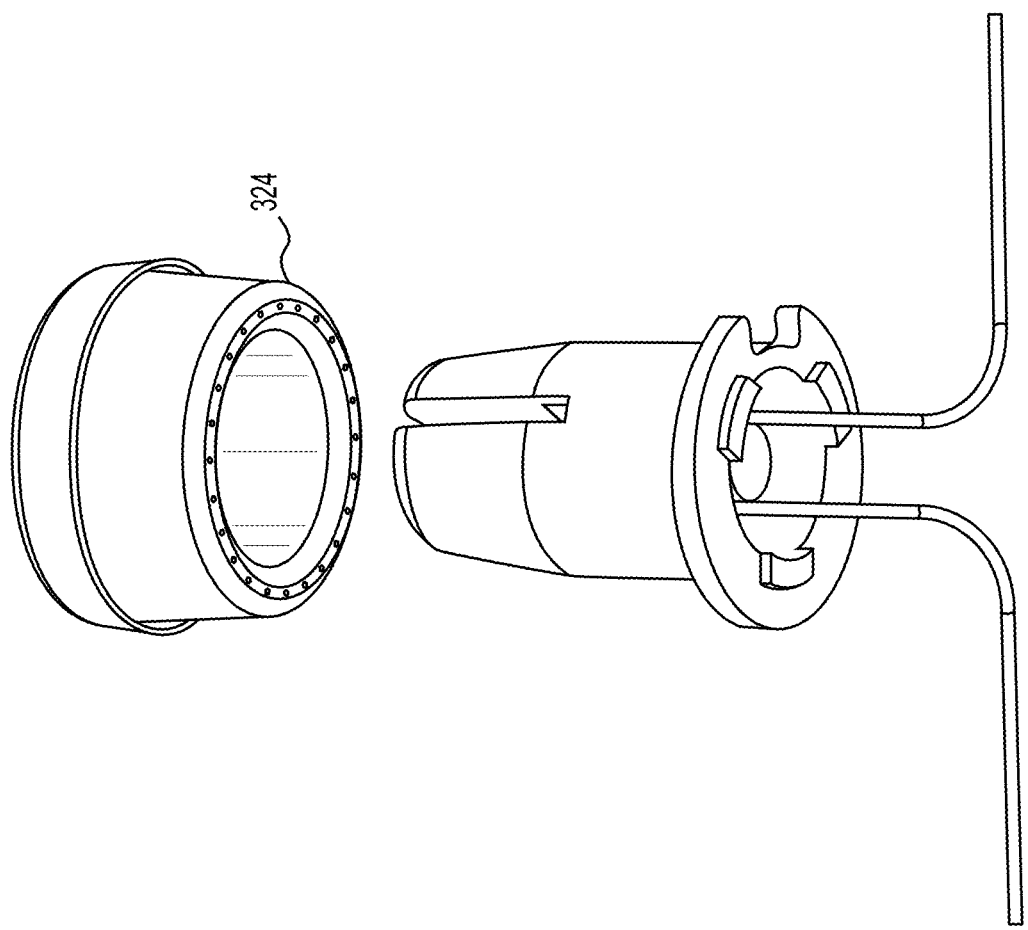

US 11,882,872 B2

CAPSULES, HEAT-NOT-BURN (HNB) AEROSOL-GENERATING DEVICES, AND METHODS OF GENERATING AN AEROSOL

BACKGROUND

Field

The present disclosure relates to capsules, heat-not-burn (HNB) aerosol-generating devices, and methods of generating an aerosol without involving a substantial pyrolysis of the aerosol-forming substrate.

Description of Related Art

Some electronic devices are configured to heat a plant material to a temperature that is sufficient to release constituents of the plant material while keeping the temperature below a combustion point of the plant material so as to avoid any substantial pyrolysis of the plant material. Such devices may be referred to as aerosol-generating devices (e.g., heat-not-burn aerosol-generating devices), and the plant material heated may be tobacco or other plant material with active ingredients. In some instances, the plant material may be introduced directly into a heating chamber of an aerosol-generating device. In other instances, the plant material may be pre-packaged in individual containers to facilitate insertion and removal from an aerosol-generating device.

SUMMARY

At least one embodiment relates to a capsule for a heat-not-burn (HNB) aerosol-generating device. In an example embodiment, the capsule may include a base of a thermally-conductive material, the base defining a first cavity therein, the base including a first surface, the first surface defining an opening to a second cavity, the first surface including a first plurality of apertures through the first surface and a cover coupled to the base and on the base, the cover including a second plurality of apertures in a middle portion of the cover, the first plurality of apertures and the second plurality of apertures defining an air flow path through the base and the cover.

In at least one example embodiment, the base further includes a first wall and a second wall, the first surface connecting the first wall and the second wall, the first surface, the first wall and the second wall defining the first cavity.

In at least one example embodiment, a width of the first cavity increases as the first wall and the second wall extend from the first surface.

In at least one example embodiment, the width continuously increases from a bottom portion to a top portion.

In at least one example embodiment, the width has a maximum of about 2 mm.

In at least one example embodiment, the first wall, the second wall and the first surface are integral.

In at least one example embodiment, the first plurality of apertures are in a circular pattern.

In at least one example embodiment, the first plurality of apertures are in a single circular line.

In at least one example embodiment, the cover includes a second surface and a third surface, the second surface and the third surface being at different heights, the second plurality of apertures being in the third surface.

In at least one example embodiment, the third surface is elevated with respect to the second surface.

In at least one example embodiment, the cover includes an overhang coupled to the base.

In at least one example embodiment, a width of the first cavity increases along a first direction and a width of the second cavity decreases along the first direction.

In at least one example embodiment, the first direction is a longitudinal direction of the capsule.

In at least one example embodiment, the second plurality of apertures are over an interior wall of the base, the interior wall defining an end of the second cavity.

In at least one example embodiment, the capsule further includes an aerosol-forming substrate in the first cavity.

In at least one example embodiment, the aerosol-forming substrate includes tobacco.

In at least one example embodiment, the second plurality of apertures are in a circular pattern including at least two circles.

At least one example embodiment provides an aerosol-generating device including a capsule, the capsule including a base of a thermally-conductive material, the base defining a first cavity therein, the base including a first surface, the first surface defining an opening to a second cavity, the first surface including a first plurality of apertures through the first surface and a cover coupled to the base and on the base, the cover including a second plurality of apertures in a middle portion of the cover, the first plurality of apertures and the second plurality of apertures defining an air flow path through the base and the cover. The aerosol-generating device further includes a heating system configured to heat the base of the capsule.

In at least one example embodiment, the heating system includes a heater and a heater sleeve covering a portion of the heater.

In at least one example embodiment, the heater sleeve is fitted to abut walls of the second cavity.

In at least one example embodiment, the aerosol-generating device further includes a biasing element to provide a force to the capsule such that the capsule contacts the heater sleeve.

In at least one example embodiment, the aerosol-generating device further includes an aerosol-forming substrate in the first cavity.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIGS. 5A-5C illustrate a capsule and a heater according to at least one example embodiment;

DETAILED DESCRIPTION

Figure 1:
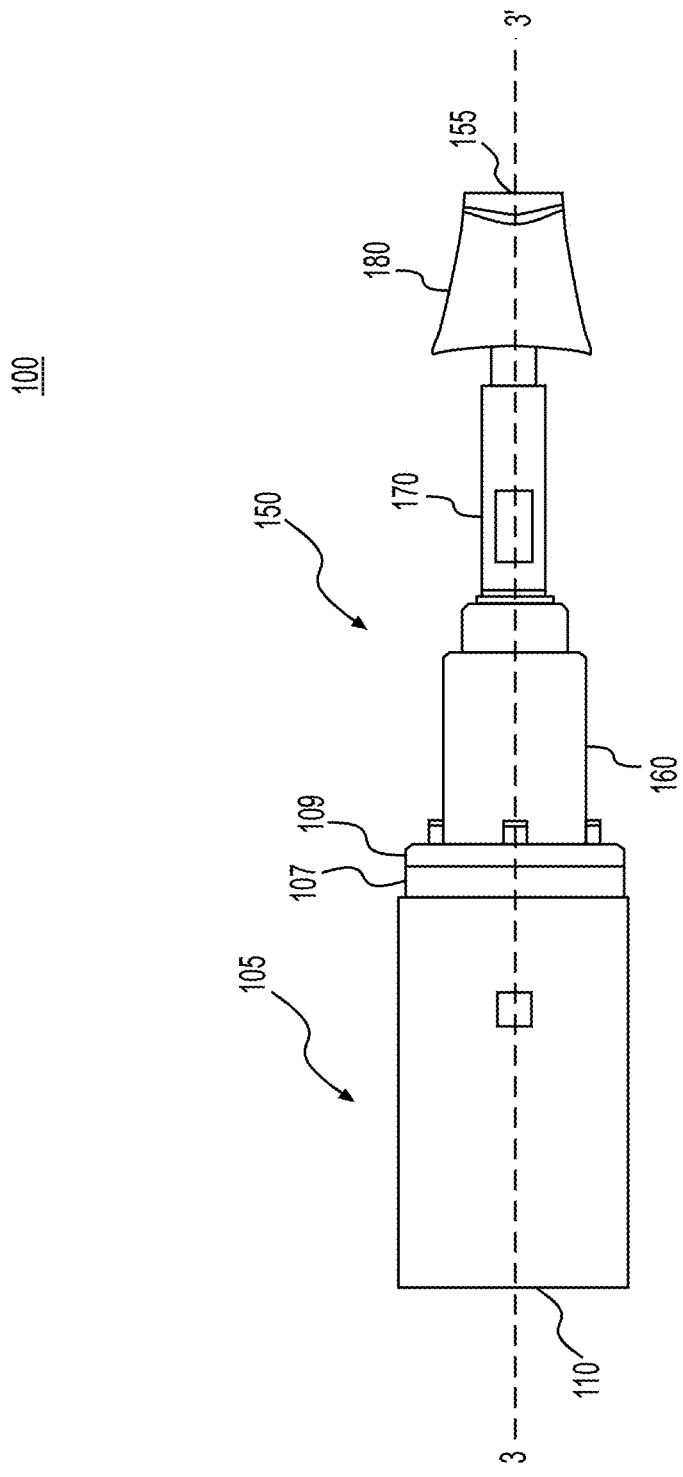
FIG. 1 illustrates an aerosol-generating device according to at least one example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," or "covering" another element or layer, it may be directly on, connected to, coupled to, attached to, adjacent to or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

When the words "about" and "substantially" are used in this specification in connection with a numerical value, it is intended that the associated numerical value include a tolerance of ±10% around the stated numerical value, unless otherwise explicitly defined.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Hardware may be implemented using processing or control circuitry such as, but not limited to, one or more processors, one or more Central Processing Units (CPUs), one or more microcontrollers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

FIG. 1 illustrates an aerosol-generating device according to at least one example embodiment.

As shown in FIG. 1, an aerosol-generating device 100 includes a first section 105 and a second section 150. The first section 105 is at a distal end 110. The sections 105, 150 may be coupled together at complimentary interfaces 107, 109 of the respective sections 105, 150. Both the first section 105 and the second section 150 may be reusable.

The complimentary interfaces 107, 109 may be any type of connector. Or the sections 105, 150 may be a single housing without the need for the interfaces 107, 109. In some example embodiments, the interfaces 107, 109 are threaded connectors. It should be appreciated that an interface 107, 109 may be any type of connector, including, without limitation, a snug-fit, detent, clamp, bayonet, sliding fit, sleeve fit, alignment fit, threaded connector, magnetic, clasp, or any other type of connection, and/or combinations thereof. In some embodiments, sections 105 and 150 may be part of the same piece without the need for interfaces 107, 109.

The second section 150 includes a first housing 160, a chimney 170 and a mouthpiece 180. The mouthpiece 180 is located at a proximal end 155.

As will be described in further detail below, a heater in the first section 105 generates an aerosol from a capsule containing plant material. The aerosol flows from the chimney 170 and out the mouthpiece 180 upon a negative pressure being applied at the mouthpiece 180.

Figure 2:
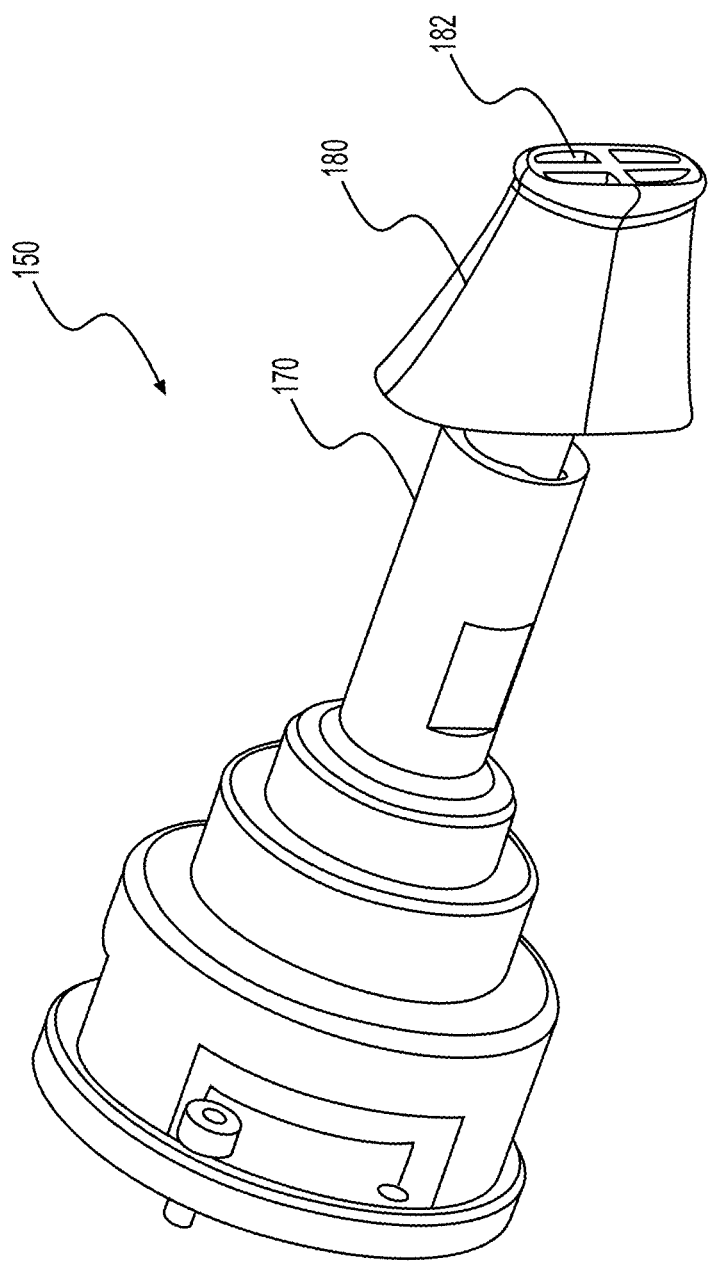
FIG. 2 is a perspective view of a second section of the aerosol-generating device of FIG. 1.

FIG. 2 illustrates a perspective view of the second section of the aerosol-generating device of FIG. 1. The mouthpiece 180 is located at an end of the chimney 170. The mouthpiece 180 includes N outlet ports 182, which may be located on-axis and/or off-axis from the longitudinal axis of the device 100. In FIG. 2, N is four, but N may be greater than or less than four. The outlet ports 182 may be angled outwardly in relation to the longitudinal axis of the device 100. The outlet ports 182 may be distributed about the mouthpiece 180 so as to align with the chimney 170. Thus, as the aerosol is drawn through the outlet ports 182, the dispersion may move in different directions.

Figure 3:
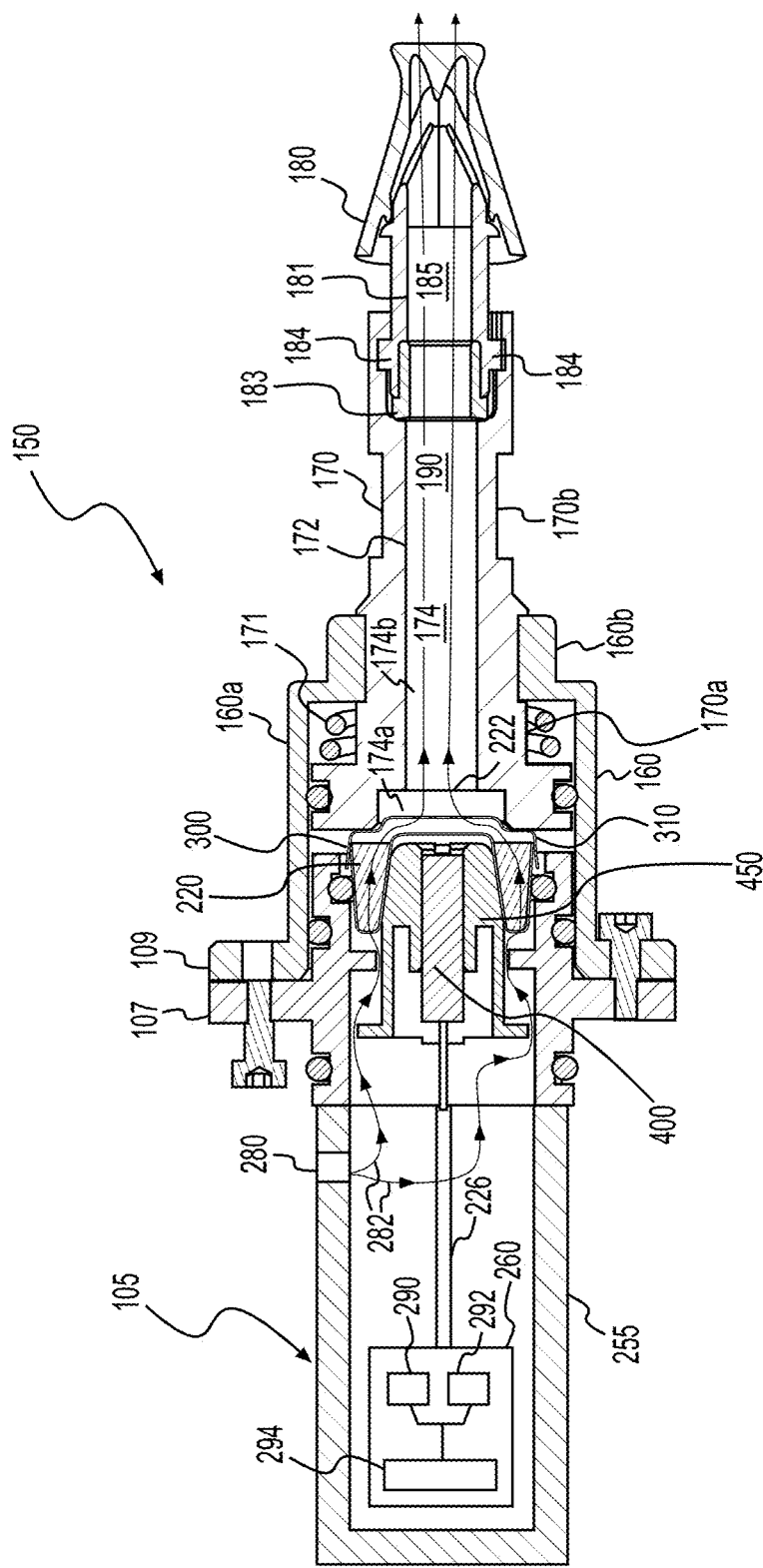
FIG. 3 illustrates a cross-sectional view of the aerosol-generating device of FIG. 1.
Figure 4:
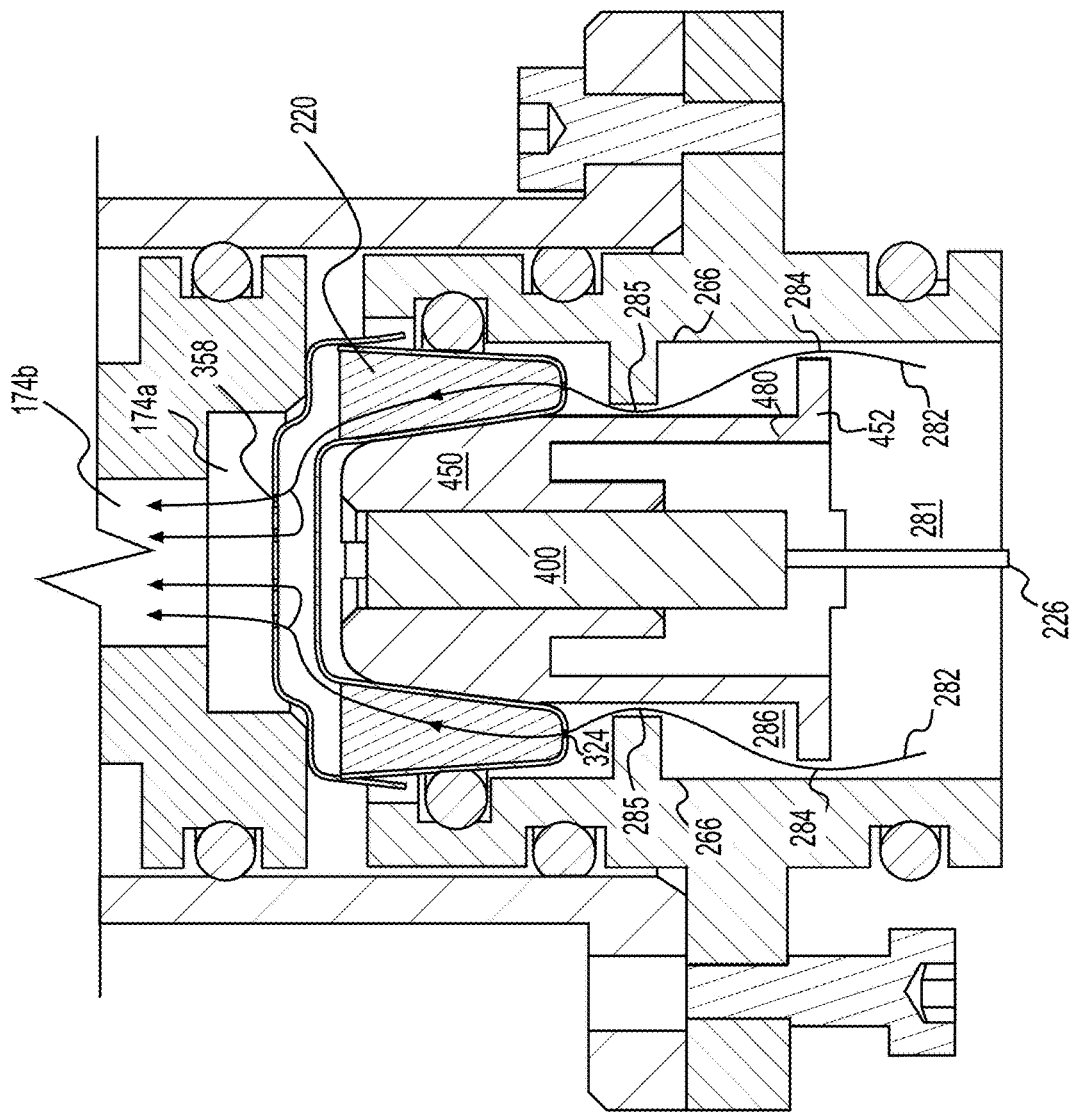
FIG. 4 illustrates a cross-sectional view of an aerosol-generating section according to at least one example embodiment.

FIG. 3 illustrates a cross-sectional view of the aerosol-generating device of FIG. 1 along the line 3-3'.

As shown in FIG. 3, the second section 150 includes the first housing 160, the chimney 170 and the mouthpiece 180. A first portion 170a of the chimney is located in the first housing 160 and a second portion 170b of the chimney 170 protrudes from the first housing 160. The second portion 170b is coupled to the mouthpiece 180. The chimney 170 includes an interior wall 172 that defines an annular space 174 having a first portion 174a and a second portion 174b. A diameter of the first portion 174a is larger than a diameter of the second portion 174b, allowing aerosol from a capsule 300 to enter the channel at the first portion 174a. The chimney 170 may be pressed against edges of a cover 310 of the capsule 300 to such that the aerosol does not flow into other portions of the first housing 160.

A spring 171 may be located in a gap between the chimney 170 and the first housing 160. The spring 171 allows the chimney 170 and the capsule 300 to maintain contact and applies a force to ensure the capsule 300 maintains contact to the heater sleeve 450. The spring 171 reduces and/or eliminates air gaps between the capsule 300 and the heater sleeve to improve heat transfer to an aerosol-forming substrate 220.

Moreover, the mouthpiece 180 includes at least one internal wall 181 that defines a space 185 through the mouthpiece 180. The annular space 174 and the space 185 for an air flow channel 190 for aerosol to travel from a capsule 300 to out of the mouthpiece 180. A filter material (to reduce temperature of the aerosol) or flavor material to enhance flavor experience may be in the space 185. The flavor material may include crushable capsules to alter flavor of the aerosol entering the space 185.

In some example embodiments, the mouthpiece 180 is inserted into two slots in the chimney 170 and then twisted 90 degrees. When the mouthpiece 180 is twisted, two tabs 184 at the bottom of the mouthpiece may be locked in place. An interference fit may force the mouthpiece 180 towards the chimney 170 and create a seal between the mouthpiece 180, a sealing element 183 (e.g., silicone) and the chimney 170.

The first section 105 includes a housing 255, a control system 260, electrical leads 226, a heater 400 and a heater sleeve 450. The housing 255 includes one or more air inlets 280 which allows air to flow along air flow paths 282.

In an example embodiment, the control system 260 includes a controller 290 that is operationally connected to a power supply 294 and at least one sensor 292, such as a pressure sensor, a flow sensor and/or a temperature sensor. The sensor(s) 292 can be located in the first section 105 or the second section 150. In an example embodiment, the at least one sensor 292 is operationally constructed to measure one or more of the following: a resistance of the heater 400, a temperature of the heater 400 and/or a draw of air flow through the aerosol-generating device 100. In an example embodiment, the controller 290 receives an input signal, or signals, from the sensor(s) 292, and the controller 290 controls operations of the aerosol-generating device 100, including supplying an electrical current from the power supply 294 to the heater 100 to heat the aerosol-generating substrate based at least in part on the signal(s) from the sensor(s) 292. In an example embodiment, the control system 260 is operationally and electrically connected to the heater 400 via the electrical leads 226 that allow the control system 260 to selectively send the electrical current to the heater 400.

The aerosol thus formed is evacuated out of the device 100 via the mouthpiece 180.

In an example embodiment, the one or more air inlets 280 are included in either in the first section 105 and/or the second section 150 of the device 100. In an example embodiment, the air inlet(s) 280 are used to establish an air flow path through the device 100 that may exit the mouthpiece 180, where the heater 400 and a capsule 300 are in, or otherwise exposed to, the air flow path. Positions of the one or more air inlets are not limited thereto. Depending on the placement of the air inlet location with respect to the heater 400, the heater 400 may pre-heat the air before air enters the capsule air inlet.

In an example embodiment, the control system 260 is in fluid communication with the air flow path.

In an example embodiment, the second section 150 is detachable from the first section 105 to allow the capsule to be placed over the heater 400 and the heater sleeve 450. For example, the second section 150 may be detached from the first section 105 by twisting off the second section 150.

In another embodiment, the capsule 300 is temporarily held in place by the heater sleeve 450 and the chimney 170, such that the capsule 300 is removable and replaceable, allowing the first section 105 and the second section 150 to be non-disposable and/or be re-used with capsules 300.

In an example embodiment, the heater 400 is in thermal communication with the capsule 300.

In an example embodiment, the heater 400 heats the aerosol-forming substrate 220 in the capsule 300 in order to produce an aerosol 222 that flows through the air flow channel 190 that exits the mouthpiece 180. In an example embodiment, the heater sleeve 450 contacts the capsules such that heat generated by the heater 400 is transferred to the capsule 300 through the heater sleeve 450. The capsule 300 is made of a heat conducting material and heats the aerosol-forming substrate 220 using the heat generated by the heater 400.

In an example embodiment, the mouthpiece 180 is permanently affixed in the chimney 170, or alternatively the mouthpiece 180 is removable.

In some example embodiments, the heater 400 warms the aerosol-forming substrate 220, but the heater 400 does not burn and/or combust the aerosol-forming substrate 220. Thus, the aerosol-forming substrate 220 in some example embodiments is non-combustible. Because the device 100 includes the heater 400 that vaporizes the aerosol-forming substrate 220, but otherwise the device 100 does not combust any material, the device 100 may be referred to as a "non-combustible device."

For example, the heater 400 may heat the aerosol-forming substrate 220 to a temperature of 125 degrees Celsius to 320 degrees Celsius and, more preferable, between 250-280 degrees Celsius. However, example embodiments are not limited thereto. For example, the heater 400 may be controlled to heat at a desired temperature based on a type of aerosol-forming substrate 220 in the capsule 300, the density of the aerosol-forming substrate in the capsule 300, additives in the aerosol-forming substrate, a sub-combination thereof or a combination thereof.

In an example embodiment, the power supply 294 is a battery, such as a lithium ion battery. The battery may be a Lithium-ion battery or one of its variants, for example a Lithium-ion polymer battery. Alternatively, the battery is a Nickel-metal hydride battery, a Nickel cadmium battery, a Lithium-manganese battery, a Lithium-cobalt battery, a fuel cell or a solar cell. Any other power sources or battery technology may be used. In an example embodiment, first section 105 may be usable until the energy in the power supply 294 of the control system 260 is depleted and/or lowered below a certain threshold. Alternatively, the power supply 294 of the control system 260 may be rechargeable and reusable, and may include circuitry allowing the battery to be chargeable by an external charging device, or may be rechargeable via solar power. In some example embodiments, the circuitry of the control system 260, when charged, may provide power for a desired (or alternatively, a determined) number of draws, until the energy in power supply 294 is depleted, and/or until the energy in power supply 294 is lowered below a certain threshold, after which the circuitry must be re-connected to an external charging device.

In some examples, air flow through the device 100 may be caused by air being drawn into the air inlet(s) 280 and through the first section 105. As will be discussed in further detail below, the air flows along paths 282, enters the capsule 300 and may become entrained (eluted) by aerosol that may be produced by the heater 400 heating the aerosol-forming substrate 220.

In an example embodiment, an air flow through the device 100 activates the device 100. The sensor(s) 292 may be configured to generate an output indicative of an air flow, a magnitude of an air flow, and/or a direction of an air flow, where the controller 290 may receive the output from the sensor(s) 292 output and determine if the following internal conditions exist: (1) a direction of the air flow indicates a draw of air flow through the device 100 (versus blowing air through the device 100), and/or (2) a magnitude of the air flow exceeds a threshold value. In some example embodiments, only one condition may be sufficient to activate the heater, while in other examples, two conditions or all conditions may have to be met before activating the heater. If these internal conditions of the device 100 are met, the controller 290 electrically connects the power supply 294 to the heater 400, thereby activating the heater 400. In an example embodiment, the sensor(s) 292 generate a variable output signal that is in at least partial correlation with a magnitude of a pressure drop sensed by the sensor(s) 292. In an example embodiment, the controller 290 may send a variable electrical current to the heater 400 based on the variable output signal from the sensor(s) 292. The sensor(s) 292 may include a sensor as disclosed in "Electronic Smoke Apparatus," U.S. application Ser. No. 14/793,453, filed on Jul. 7, 2015, or a sensor as disclosed in "Electronic Smoke," U.S. Pat. No. 9,072,321, issued on Jul. 7, 2015, each of which are hereby incorporated by reference in their entirety into this document. Other type of sensors to detect an air flow may be used.

FIG. 4 illustrates a cross-sectional view of an aerosol-generating section according to at least one example embodiment.

As shown in FIG. 4, air long the air flow paths 282 enters the device 100 through the inlet 280 upon a negative pressure being applied at the mouthpiece 180. Air enters a channel 281 that is upstream from the heater 400 along the air flow paths 282.

Air along the air flow paths proceeds around the heater sleeve 450 in a gap 284. The gap 284 is a space between the housing 255 and the heater sleeve 450. As shown in FIG. 4, the heater sleeve 450 includes a circular base 452. A diameter of the circular base 452 may be larger than a diameter of a continuous wall 480 of the heater sleeve 450. The continuous wall 480 may extend from the circular base 452 at a normal angle or an angle less than 90 degrees. Due to the differences in diameter between the circular base 452 and the continuous wall 480, air along air flow paths 282 exit into an area 286 of the channel 281 that is between the housing 255 and the heater sleeve 450. As air passes along the continuous wall 480, as well as through the area 286, the air may be heated by the heater sleeve 450 as the heater sleeve 450 conducts heat generated by the heater 400.

From the area 286, air flows through a gap 285. The housing 255 includes a protrusion 266. The protrusion 266 protrude into an interior of the housing 255 to narrow the channel 281. The gap 285 is between the protrusion 266 and the heater sleeve 450 and may be smaller than the gap 284. More specifically, a distance between the housing 255 and the circular base 452 may be greater than a distance between the protrusion 266 and the continuous wall 480.

In other example embodiments, the protrusion 266 may be an alignment tab and the gap between the protrusion 266 and the heater sleeve 450 and may be larger than the gap 284.

Air exits the gap 284 and enters the capsule 300 through apertures 324. The heater 400 is capable of heating the aerosol-forming substrate 220 to an extent that the flavoring, nicotine and/or ingredients in the aerosol-forming substrate 220 is at least partially extracted (e.g., aerosolized) to create the aerosol 222 that is extracted from aerosol-forming substrate 220. The heater 400 heats the capsule 300 and the aerosol-forming substrate 220 to an extent that the aerosol-forming substrate 220 and the flavoring, nicotine and/or other materials of the aerosol-forming substrate 220 remain below a combustion temperature.

Consequently, the air mixes with the aerosol-forming substrate 220 to form an aerosol 222 that exists the capsule 300 through apertures 358 into the first portion **174*a* and then the second portion 174*b* of the chimney 170**.

FIG. 5A illustrates a cross-sectional view of a capsule and a heater according to at least one example embodiment. FIGS. 5B-5C are perspective views of the capsule and the heater of FIG. 5A according to at least one example embodiment.

Although the capsule 300 is shown as resembling a cylinder with an elevated portion, it should be understood that other configurations may be employed. For instance, the shape may be a disc such that the capsule 300 has a disk-like appearance. In another instance, the shape of the capsule 300 may be box-like. In other instances, the capsule 300 may have a polygonal shape (regular or irregular), including a triangle, a rectangle (e.g., square), a pentagon, a hexagon, a heptagon, or an octagon. The structure of the capsule 300 may facilitate stacking so as to allow a plurality of capsules to be stored in an aerosol-generating device or other receptacle for dispensing a new capsule or receiving a depleted capsule.

The capsule 300 includes a base 305 and a cover 310. The base 305 and the cover 310 may include a suitable heat conducting material such as aluminum, an aluminum alloy, stainless steel, copper alloy or a combination thereof. The base 305 and the cover 310 may be made of the same material or different materials. For example, the cover 310 may be made of a nonconductive material while the base 305 is made of a heat conducting material. The base 305 and the cover 310 are connected via a connecting interface 311. The connecting interface 311 may be along an exterior surface 312 of the base 305 and/or along an interior surface 360 of the cover 310. The connecting interface 311 may be a snap-fit connection or friction fit connection, for example. In other example embodiments, the base 305 and the cover 310 may be connected by "rolling" the overhang 350 of the cover 310 over the base 305 or welding the base 305 and the cover 310 together.

In some example embodiments, the base 305 and the cover 310 form an integral piece to reduce tampering by rolling the overhang 350 of the cover 310 over the base 310 in a manner such that attempts to take the cover 310 off would damage the base 305.

The base 305 includes the exterior side 312, a bottom side 314 and an interior side 316. The exterior side 312, the bottom side 314 and the interior side 316 may be a single piece or each may be separate pieces connected together. The interior side 316 extends from the bottom side 314 to an interior top side 318. The interior side 316 and the interior top side 318 define a cavity 320. The interior side 316 wraps around to define a diameter of the cavity and is angled such that a diameter of the cavity 320 decreases from the bottom side 314 to the top side 318. In example embodiments, when describing the base 305 and the cover 310, a side may also be referred to as a wall.

Figure 5B:
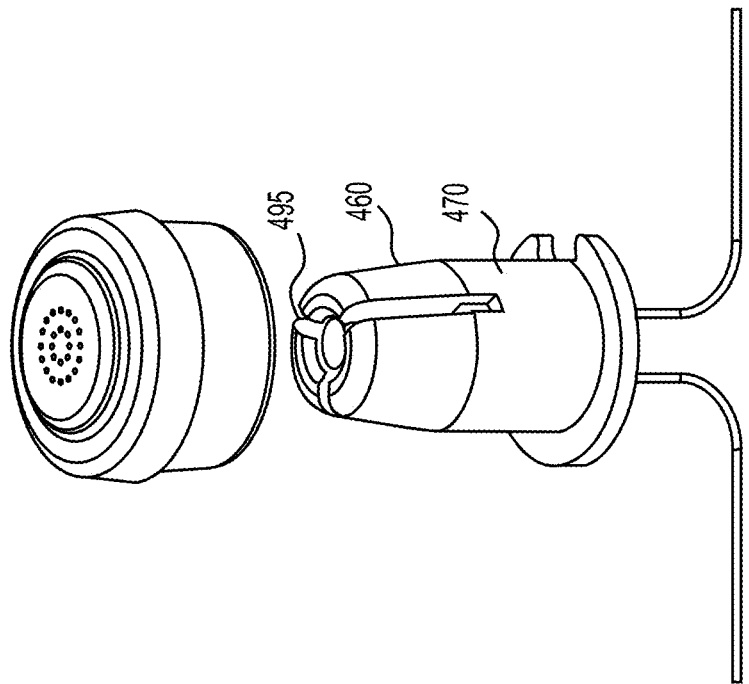
Figure 5A:
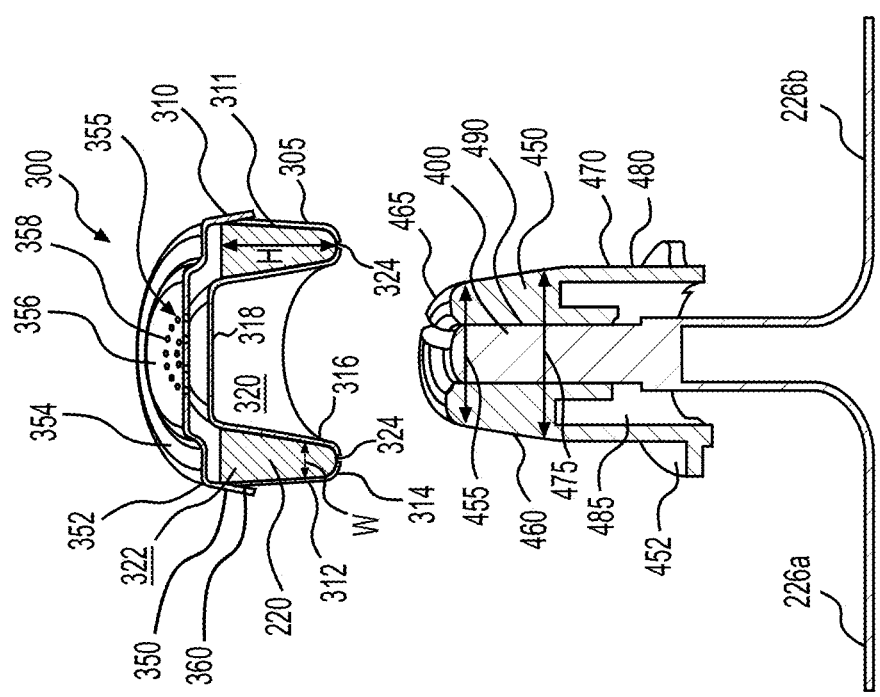

As shown in FIG. 5A, the cavity 320 may be annular. However, the interior side 316 may be shaped and angled differently such that the cavity 320 is a different shape. The interior side 316 is shaped such as to allow a cover from another capsule to fit in at least a portion of the cavity 320 so multiple capsules may be stacked.

The exterior side 312, the bottom side 314 and the interior side 316 define a cavity 322 for containing an aerosol-forming substrate 220.

The interior side 316 is angled away from the exterior side 312 from the bottom side 314 to the top side 318 such that a width of the cavity 322 continuously increases from the bottom side 314 to the top side 318. In an example embodiment, the wall thickness of the interior side 316 is 0.2 mm. Thus, a portion of the aerosol-forming substrate 220 may be 0.2 mm away from a heater sleeve 450.

The cross side of the cavity 322 of the aerosol-forming substrate relative to the heater contact area is kept thin and uniform. In some example embodiments, a widest part of the cavity 322 is between 1-2 mm. This allows for consistent and uniform heating of the aerosol-forming substrate 220.

The interior side 316 may be angled to create a uniform contact with tapered side 460 of the heater sleeve 450.

In some example embodiments, the width W is 50% greater at the top side 318 than at the bottom side 314. For example, the width W at the bottom side 314 may be 1 mm and the width W at the top side is 1.5 mm.

However, example embodiments are not limited thereto. For example, the cavity 322 may have a constant width W and the exterior side 312 in the interior side 316 may be parallel. The exterior side 312 and the interior side 316 wrap around the cavity 320 in such a manner that for each distance along a height H, the width W is constant.

In some example embodiments, a same cross-sectional profile of the aerosol-forming substrate 220 is achieved when the exterior side 312 and the interior side 316 are parallel, but a thickness of wall of the interior side 316 constantly changes along the height H.

In some example embodiments, the exterior side 312 is anodized to reduce heat loss and improve energy efficiency. Alternatively or additionally, the bottom side 314 may be anodized. Alternatively or additionally, portions of the cap 310 may be anodized.

As shown in FIGS. 5A and 5C, the bottom side 314 includes a plurality of apertures 324 arranged around the bottom side 314. The holes 324 may be equidistant apart. However, example embodiments are not limited thereto. The number of apertures may be based on a computational fluid dynamics analysis.

The apertures 324 allow air to enter the capsule 300. More specifically, air enters through the aperture 324 and flows through the aerosol-forming substrate 220 in the cavity 322.

The apertures 324 are sized such that the aerosol-forming substrate do not fall out of the apertures and may not be pulled out of the capsule. In some example embodiments, a diameter of the apertures 324 is 0.3 mm. In other example embodiments, the diameter of the apertures 324 may be larger or smaller depending on the particle size of the aerosol-forming substrate 220 inside the capsule 300.

As discussed herein, an aerosol-forming substrate is a material or combination of materials that may yield an aerosol. An aerosol relates to the matter generated or output by the devices disclosed, claimed, and equivalents thereof. The material may include a compound (e.g., nicotine, cannabinoid), wherein an aerosol including the compound is produced when the material is heated. The heating may be below the combustion temperature so as to produce an aerosol without involving a substantial pyrolysis of the aerosol-forming substrate or the substantial generation of combustion byproducts (if any). Thus, in an example embodiment, pyrolysis does not occur during the heating and resulting production of aerosol. In other instances, there may be some pyrolysis and combustion byproducts, but the extent may be considered relatively minor and/or merely incidental.

The aerosol-forming substrate may be a fibrous material. For instance, the fibrous material may be a botanical material. The fibrous material is configured to release a compound when heated. The compound may be a naturally occurring constituent of the fibrous material. For instance, the fibrous material may be plant material such as tobacco, and the compound released may be nicotine. The term "tobacco" includes any tobacco plant material including tobacco leaf, tobacco plug, reconstituted tobacco, compressed tobacco, shaped tobacco, or powder tobacco, and combinations thereof from one or more species of tobacco plants, such as *Nicotiana rustica* and *Nicotiana tabacum*.

In some example embodiments, the tobacco material may include material from any member of the genus *Nicotiana*. In addition, the tobacco material may include a blend of two or more different tobacco varieties. Examples of suitable types of tobacco materials that may be used include, but are not limited to, flue-cured tobacco, Burley tobacco, Dark tobacco, Maryland tobacco, Oriental tobacco, rare tobacco, specialty tobacco, blends thereof, and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass. Furthermore, in some instances, the tobacco material may be mixed and/or combined with at least one of propylene glycol, glycerin, sub-combinations thereof, or combinations thereof.

The compound may also be a naturally occurring constituent of a medicinal plant that has a medically-accepted therapeutic effect. For instance, the medicinal plant may be a *cannabis* plant, and the compound may be a cannabinoid. Cannabinoids interact with receptors in the body to produce a wide range of effects. As a result, cannabinoids have been used for a variety of medicinal purposes (e.g., treatment of pain, nausea, epilepsy, psychiatric disorders). The fibrous material may include the leaf and/or flower material from one or more species of *cannabis* plants such as *Cannabis sativa, Cannabis indica*, and *Cannabis ruderalis*. In some instances, the fibrous material is a mixture of 60-80% (e.g., 70%) *Cannabis sativa* and 20-40% (e.g., 30%) *Cannabis indica*.

Examples of cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (THC) and cannabidiol (CBD), respectively, via heating. In an example embodiment, heat from the first heater 110 and/or the second heater 120 may cause decarboxylation so as to convert the tetrahydrocannabinolic acid (THCA) in the capsule 100 to tetrahydrocannabinol (THC), and/or to convert the cannabidiolic acid (CBDA) in the capsule 100 to cannabidiol (CBD).

In instances where both tetrahydrocannabinolic acid (THCA) and tetrahydrocannabinol (THC) are present in the capsule 100, the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC) during the heating of the capsule 100. Similarly, in instances where both cannabidiolic acid (CBDA) and cannabidiol (CBD) are present in the capsule 100, the decarboxylation and resulting conversion will cause a decrease in cannabidiolic acid (CBDA) and an increase in cannabidiol (CBD). At least 50% (e.g., at least 87%) of the cannabidiolic acid (CBDA) may be converted to cannabidiol (CBD) during the heating of the capsule 300.

Furthermore, the compound may be or may additionally include a non-naturally occurring additive that is subsequently introduced into the fibrous material. In one instance, the fibrous material may include at least one of cotton, polyethylene, polyester, rayon, combinations thereof, or the like (e.g., in a form of a gauze). In another instance, the fibrous material may be a cellulose material (e.g., non-tobacco and/or non-*cannabis* material). In either instance, the compound introduced may include nicotine, cannabinoids, and/or flavorants. The flavorants may be from natural sources, such as plant extracts (e.g., tobacco extract, *cannabis* extract), and/or artificial sources. In yet another instance, when the fibrous material includes tobacco and/or *cannabis*, the compound may be or may additionally include one or more flavorants (e.g., menthol, mint, vanilla). Thus, the compound within the aerosol-forming substrate may include naturally occurring constituents and/or non-naturally occurring additives. In this regard, it should be understood that existing levels of the naturally occurring constituents of the aerosol-forming substrate may be increased through supplementation. For example, the existing levels of nicotine in a quantity of tobacco may be increased through supplementation with an extract containing nicotine. Similarly, the existing levels of one or more cannabinoids in a quantity of *cannabis* may be increased through supplementation with an extract containing such cannabinoids.

In an example embodiment, the cavity 322 may contain 200-300 mg of tobacco and preferably between 200-230 mg.

Referring back to FIG. 5A, the cover 310 may include an overhang section 350 which provides the connection at the connection interface 311 to the base 305.

In some example embodiments, the overhang section 350 provides a press fit between the cover 310 and the base 305. The overhang 350 permits the cover 310 to be removed from the base 305.

In other example embodiments, the overhang 350 of the cover 310 is rolled over the base 305 in a manner such that attempts to take the cover 310 off would damage the base 305.

The overhang 350 extends from a middle portion of the base 305 in transitions to a lower planar surface 354 at a curve 352. When the cover 310 is placed over the base 305 the lower planar surface 354 extends from the curve inward over the cavity 322. The lower planar surface 354 transitions to an elevated planar surface 356. When the cover 310 is placed over the base 305, the elevated planar surface 356 is higher than the lower planar surface 354 (is at a farther distance from the base 305) and is over the top side 318 of the base 305. Moreover, the lower planar surface 354 transitions to the elevated planar surface 356 over the cavity 322.

The elevated planar surface 356 includes a plurality of apertures 358 in a middle portion 359 of the elevated planar surface 356. A number of the apertures 358 may be based on empirical data and/or computation fluid dynamics analysis. The apertures 358 are sized such that the aerosol-forming substrate do not fall out of the apertures and may not be pulled out of the capsule. In some example embodiments, a diameter of the aerosol exit apertures 358 are 0.3 mm. In other example embodiments, the diameters of the apertures 358 may be larger or smaller depending on the particle size of the aerosol-forming substrate 220 inside the capsule 300. The apertures 358 allow aerosol generated from heating the aerosol-forming substrate 220 to exit the capsule 300. In some example embodiments, the size and number of apertures 358 is the same as the size and number of apertures 324. The size of the apertures 324 and 358 are sized to prevent the aerosol-forming substrate from exiting the capsule 300.

A heater 400 may be a ceramic cartridge heater that heats the capsule 300 through conduction. The heater is cylindrically shaped and is connected to wires 226a and 226b to receive power from the power source 294 via the controller 290.

The heater 400 is configured to heat the aerosol-forming substrate. As a result of the heating, the temperature of the aerosol-forming substrate may increase, and an aerosol may be generated.

In an example embodiment, the heater 400 is configured to undergo Joule heating (which is also known as ohmic/resistive heating) upon the application of an electric current thereto. Stated in more detail, the heater 400 may be formed of conductors (same or different) and configured to produce heat when an electric current passes through the conductors. The electric current may be supplied from the power source 294 within the aerosol-generating device. Suitable conductors for the heater 400 include an iron-based alloy (e.g., stainless steel) and/or a nickel-based alloy (e.g., nichrome). In some example embodiments, the heater 400 is cylindrical. The resistance of the heater 400 may be 1 ohm and the diameter of the heater 400 is about 2 mm with a length of about 15 mm. Furthermore, although the heater 400 is shown in FIGS. 5A-5C, it should be understood that, in some example embodiments, the heater 400 may be a different shape.

The electric current from the power source may be transmitted via electrodes/wires 226a and 226b connected to the heater 400. Furthermore, the supply of the electric current from the aerosol-generating device to the heater 400 may be a manual operation (e.g., button-activated) or an automatic operation (e.g., puff-activated).

A heater sleeve 450 covers portions of the heater 400 and is designed to be inserted into the cavity 320. In some example embodiments, the heater sleeve 450 may be made of aluminum. More specifically, an upper diameter 455 of the heater sleeve 450 is less than a diameter of the top side 318 of the base 305 of the capsule 300. The heater sleeve 450 includes the tapered section 460 that extends from a top surface 465 of the heater sleeve 450 to a lower portion 470. The tapered section 460 is angled such that a diameter continuously increases from the top surface 465 to the lower portion 470. Thus, a diameter 475 is greater than the diameter 455.

An exterior surface of the tapered section 460 is tapered such that it angled in the same manner as the interior side 316. This allows the tapered section 460 to contact the interior side 316 when the heater 400 and the heater sleeve 450 are inserted into the cavity 320. The addition of the spring pressure from the top promotes contact between the tapered surface 460 and the interior side 316.

The lower portion 470 includes a continuous wall 480 defining a cavity 485. The lower portion 470 includes a constant diameter.

The heater sleeve 450 further includes a bore 490 extending from the top surface 465 to the cavity 485. The bore 490 is dimensioned to allow the heater 400 to be inserted in the bore 490 such that the heater 400 is exposed at the top surface 465 when inserted into the bore 490.

Furthermore, the heater sleeve 450 includes slots 495 that extend from the top surface 465 into the lower portion 470. While the number of slots 495 is three as shown in FIGS. 5A-5C, example embodiments are not limited thereto. The slots 495 permit the heater sleeve 450 to expand to accept the insertion of the heater 400, resulting in a pressure applied to the heater 400 to keep it in place.

The sleeve 450 acts as a collet to the heater 400. When the heater 400 is inserted into the heater sleeve 450, the slots 495 that have been machined away in the heater sleeve 450 are allowed to expand to accept the heater 400 while still applying light pressure to the heater 400, promoting contact and heat transfer between the heater sleeve 450 and the heater 400.

Figure 6:
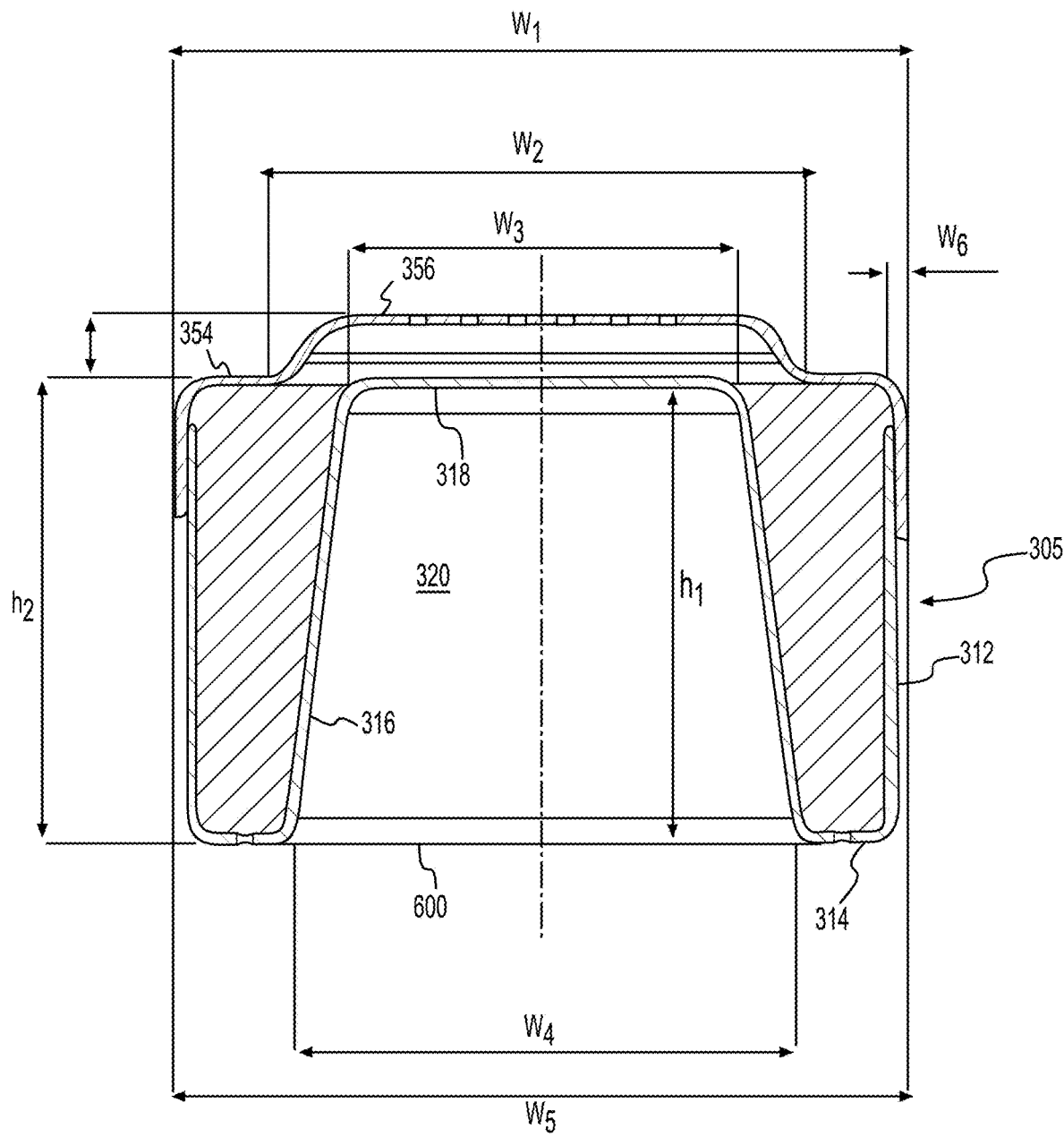
FIG. 6 illustrates a cross section view of a capsule according to at least one example embodiment.

FIG. 6 illustrates a cross section view of a capsule according to at least one example embodiment. As shown in FIG. 6, a depth $h_1$ of the cavity 320 may be 7.95 mm. More specifically, the depth $h_1$ extends from the top side 318 to a common plane 600 between of the cavity 320 and the bottom side 314. A depth $h_2$ is the distance between the lower planar surface 354 and the bottom side 314. The depth $h_2$ may be 8.00 mm.

A width $w_1$ (i.e., the diameter) of the cover 310 may be 12.30 mm and a width $w_2$ of the elevated planar surface 356 including the transition portion to the lower planar surface 354 may be 9.31 mm. The design of the transition portion from the lower planar surface 354 to the elevated planar surface 356 guides the aerosol back to a central axis of the chimney 170.

A width $w_3$ is a diameter of the top side 318 and may be 6.61 mm. The width $w_3$ may also be considered the smallest the diameter of the cavity 320. A width $w_4$ is a diameter the cavity 320 defined by the bottom side 314. The width $w_4$ may be 8.39 mm and may be the largest diameter of the cavity 320. A width $w_5$ is a width of the base 305 and is a diameter of the exterior side. The width $w_5$ may be 12.00 mm.

A width $w_6$ is a thickness of sides and surfaces of the base 305 and the cover 310 walls such as the exterior side 312, the interior side 316, the bottom side 314, the lower planar surface 354 and the elevated planar surface 356. The width $w_6$ may be 0.15 mm. In some example embodiments, all walls of the capsule 300 have uniform thickness, permitting a simplification of manufacturing.

Figure 7:
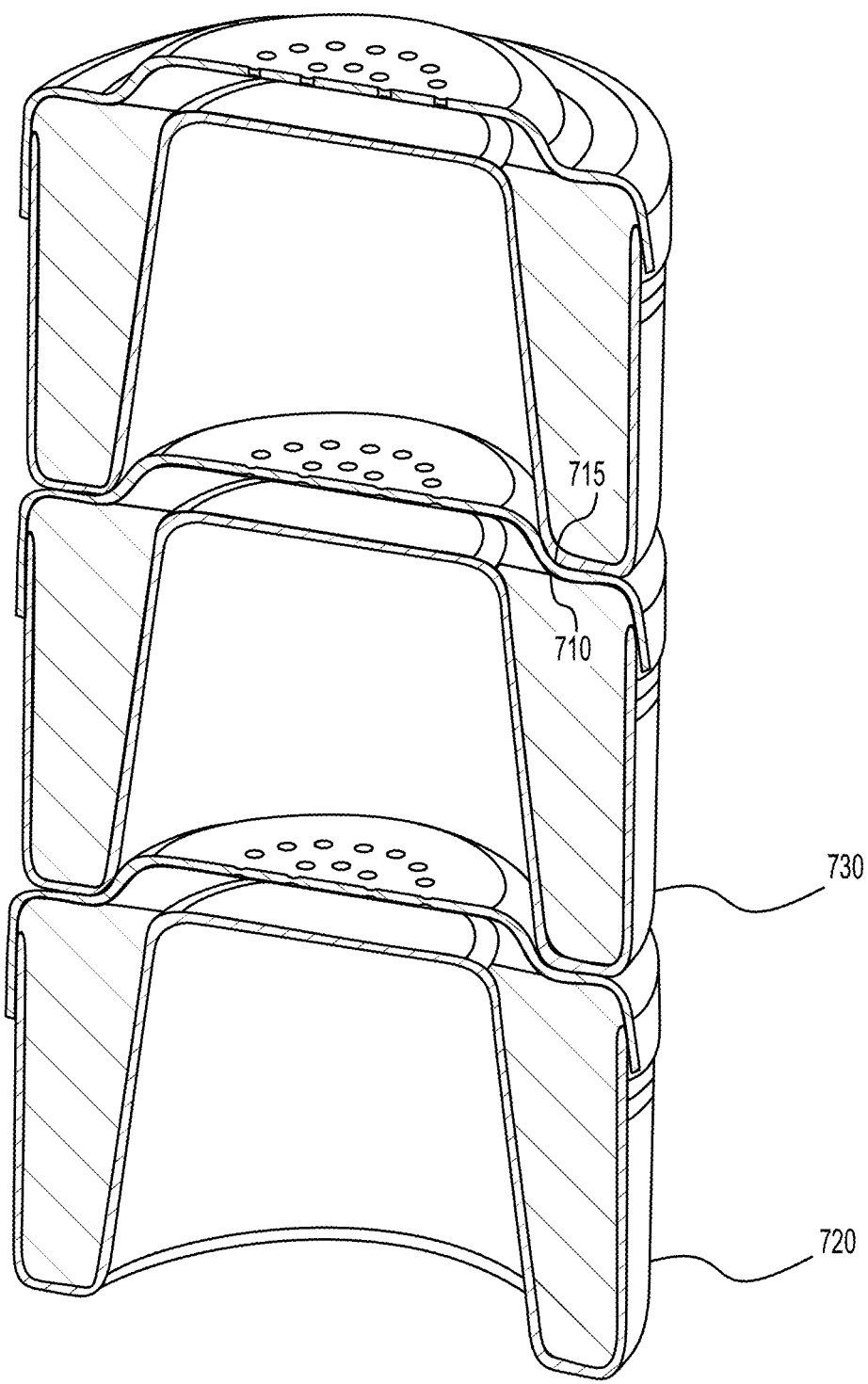
FIG. 7 illustrates a plurality of stacked capsules according to at least one example embodiment.

FIG. 7 illustrates a plurality of stacked capsules according to at least one example embodiment. As shown in FIG. 7, an initial transition 710 between the lower planar surface 354 and the elevated planar surface 356 may be a same shape as a transition 715 between the bottom side 314 and the interior side 316. Thus, when a plurality of capsules are stacked an initial transition 710 of a first capsule 720 may match a transition 715 of a second capsule 730. The initial transition 710 and the transition 715 may contact each other and a lower planar surface 354 of the first capsule 720 may contact a bottom side 314 of the second capsule 730. In addition, the elevated planar surface 356 of the first capsule 720 may protrude into a cavity 320 of the second capsule 730.

As a result, when the plurality of capsules are stacked, the stacked capsules may form a tessellation.

Figure 8:
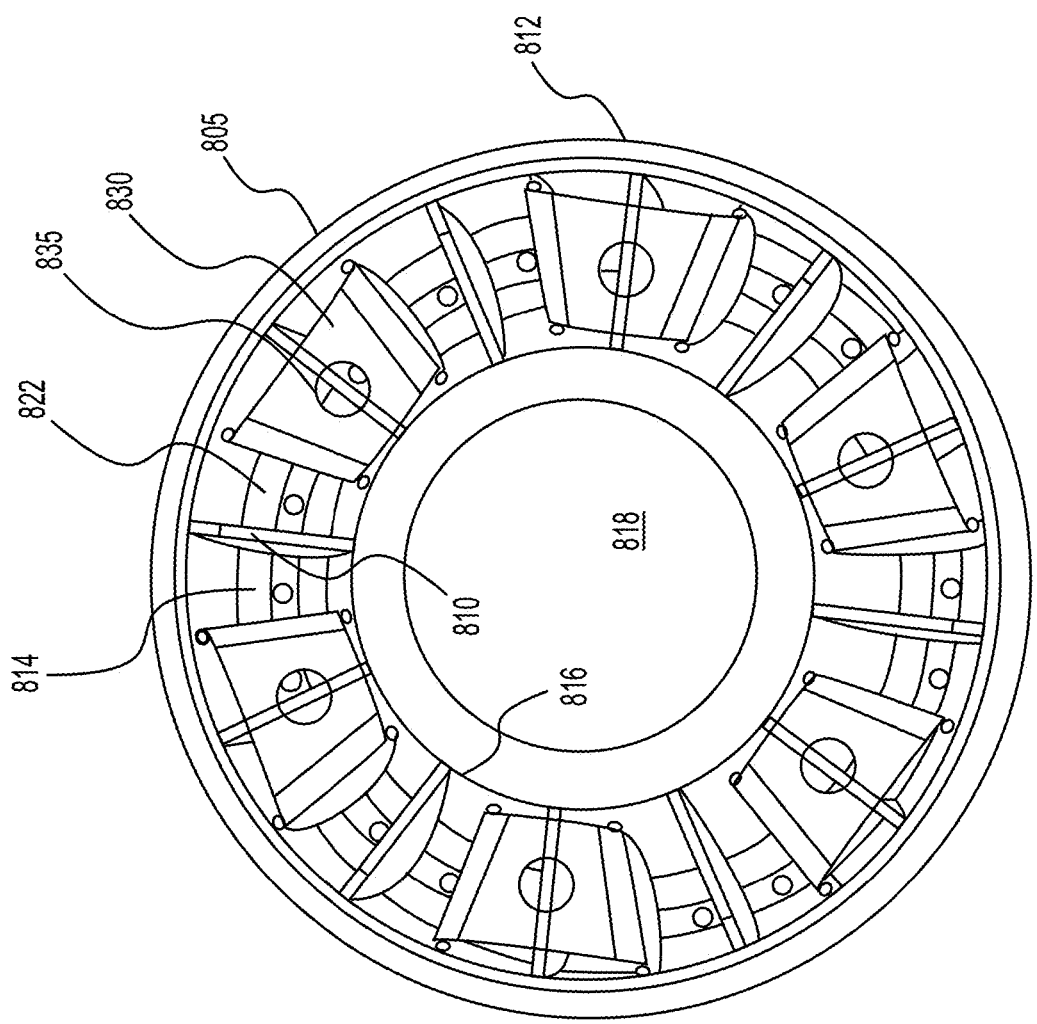
FIG. 8 illustrates a capsule according to at least one example embodiment.

FIG. 8 illustrates at least one example embodiment of cavity of a capsule.

As shown in FIG. 8, a base 805 of a capsule may include a plurality of dividers 810 in a cavity 822. Similar to the capsule described in FIGS. 3-7, the cavity 822 is defined by a bottom side 814, an exterior side 812 and an interior side 816. The bottom side 814, the exterior side 812 and the interior side 816 may be walls of the cavity 822.

The dividers 810 may extend between the exterior side 812 and the interior side 816 and down to the bottom side 814. The divider 810 may be equidistant apart or may be placed in accordance with a desired air flow through the cavity 822.

In some example embodiments, plates 830 may extend across a plurality of dividers 810 and on the plurality of dividers. The plates 830 may include an aperture 835. In FIG. 8, the plates 830 are shaped like a trapezoid, however, a shape of the plates 830 are not limited thereto. For example, the shapes of the plates may be any shape and may be based on a desired air flow through the cavity 822.

Figure 9B:
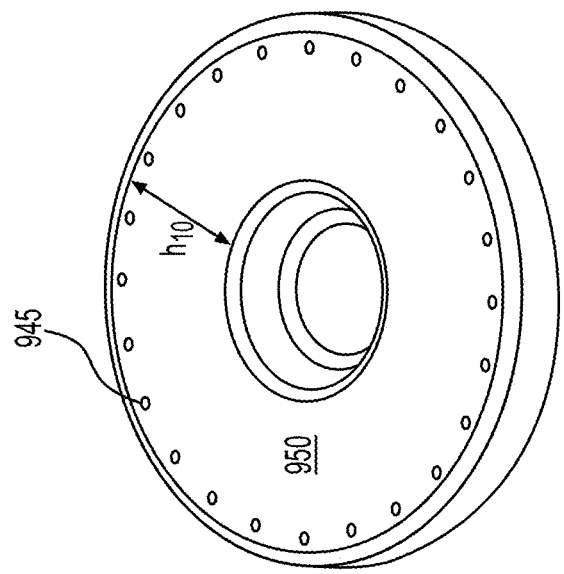
FIGS. 9A-9B illustrate a capsule according to at least one example embodiment.
Figure 9A:
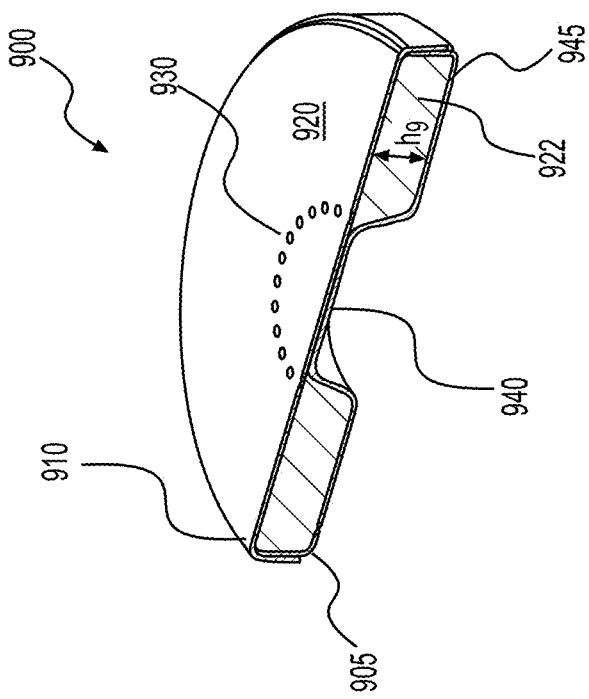

FIGS. 9A-9B illustrate a capsule according to at least one example embodiment.

FIG. 9A illustrates a cross-sectional plane view of a capsule 900. The capsule 900 is similar to the capsule 300. Thus, differences between the capsule 900 and the capsule 300 will be described. The capsule 900 includes a base 905 and a cover 910. Unlike the cover 310, the cover 910 may be have a complete flat surface 920. The base 905 defines a cavity 922 (similar to how the cavity 322 is defined). The cavity 922 is width than the cavity 322 and has a depth $h_9$ that is smaller than the depth of the cavity 322. The depth $h_9$ may be 2 mm and the cavity 922 have a total volume of 0.43 cm$^3$ to hold an aerosol-forming substrate.

Apertures 930 extend through the cover 910 and are over the cavity 922. The base 905 and the cover 910 may be spot welded at 940. In other example embodiments, the cover 910 and the base 905 may be joined at 940 by other joining methods.

FIG. 9B illustrates a bottom view of the capsule 900. As shown in FIG. 9B, the base 905 includes a plurality of apertures 945 extending through a bottom surface 950. A width $h_{10}$ of the bottom surface 950 may be greater than a width of the bottom side 314.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A capsule for an aerosol-generating device, comprising:
a base of a thermally-conductive material, the base defining a first cavity therein, the base including a first surface, the first surface defining an opening to a second cavity, the first surface including a first plurality of apertures through the first surface, the first plurality of apertures being around the opening to the second cavity, the second cavity being annular and the first cavity surrounding the second cavity; and
a cover coupled to the base and on the base, the cover including a second plurality of apertures in a middle portion of the cover, the first plurality of apertures and the second plurality of apertures defining an air flow path through the base and the cover;
wherein the second cavity is configured to receive a heating system configured to heat the base.

2. The capsule of claim 1, wherein the base further includes:
a first wall; and
a second wall, the first surface connecting the first wall and the second wall, the first surface, the first wall and the second wall defining the first cavity.

3. The capsule of claim 2, wherein a width of the first cavity increases as the first wall and the second wall extend from the first surface.

4. The capsule of claim 3, wherein the width continuously increases from a bottom portion to a top portion.

5. The capsule of claim 4, wherein the width has a maximum of about 2 mm.

6. The capsule of claim 2, wherein the first wall, the second wall and the first surface are integral.

7. The capsule of claim 1, wherein the first plurality of apertures are in a circular pattern.

8. The capsule of claim 7, wherein the first plurality of apertures are in a single circular line.

9. The capsule of claim 1, wherein the cover includes,
a second surface, and
a third surface, the second surface and the third surface being at different heights, the second plurality of apertures being in the third surface.

10. The capsule of claim 9, wherein the third surface is elevated with respect to the second surface.

11. The capsule of claim 1, wherein the cover includes an overhang coupled to the base.

12. The capsule of claim 1, wherein a width of the first cavity increases along a first direction and a width of the second cavity decreases along the first direction.

13. The capsule of claim 12, wherein the first direction is a longitudinal direction of the capsule.

14. The capsule of claim 1, wherein the second plurality of apertures are over an interior wall of the base, the interior wall defining an end of the second cavity.

15. The capsule of claim 1, further comprising:
an aerosol-forming substrate in the first cavity.

16. The capsule of claim 15, wherein the aerosol-forming substrate includes tobacco.

17. The capsule of claim 1, wherein the second plurality of apertures are in a circular pattern including at least two circles.

18. An aerosol-generating device comprising:
a capsule, the capsule including,
a base of a thermally-conductive material, the base defining a first cavity therein, the base including a first surface, the first surface defining an opening to a second cavity, the first surface including a first plurality of apertures through the first surface, the first plurality of apertures being around the opening to the second cavity, and
a cover coupled to the base and on the base, the cover including a second plurality of apertures in a middle portion of the cover, the first plurality of apertures and the second plurality of apertures defining an air flow path through the base and the cover; and
a heating system configured to be inserted into the second cavity and to heat the base of the capsule.

19. The aerosol-generating device of claim 18, wherein the heating system includes,
a heater; and
a heater sleeve covering a portion of the heater.

20. The aerosol-generating device of claim 19, wherein the heater sleeve is fitted to abut walls of the second cavity.

21. The aerosol-generating device of claim 20, further comprising:
a biasing element to provide a force to the capsule such that the capsule contacts the heater sleeve.

22. The aerosol-generating device of claim 18, further comprising:
an aerosol-forming substrate in the first cavity.

\* \* \* \* \*